United States Patent [19]
Greff

[11] Patent Number: 6,059,766
[45] Date of Patent: May 9, 2000

[54] GYNECOLOGIC EMBOLOTHERAPY METHODS

[75] Inventor: Richard J. Greff, St. Pete Beach, Fla.

[73] Assignee: Micro Therapeutics, Inc., Irvine, Calif.

[21] Appl. No.: 09/032,636

[22] Filed: Feb. 27, 1998

[51] Int. Cl.[7] .................................................. A61M 31/00
[52] U.S. Cl. ......................... 604/515; 604/508; 604/506; 604/264
[58] Field of Search .................................... 604/264, 500, 604/506–508, 514, 515, 272, 275, 279

[56] References Cited

U.S. PATENT DOCUMENTS

| | | |
|---|---|---|
| 3,527,224 | 9/1970 | Rabinowitz et al. . |
| 3,591,676 | 7/1971 | Hawkins et al. . |
| 3,875,939 | 4/1975 | Bolduc et al. . |
| 5,580,568 | 12/1996 | Greff et al. . |
| 5,630,797 | 5/1997 | Diedrich et al. ........................... 604/55 |
| 5,667,767 | 9/1997 | Greff et al. . |
| 5,695,480 | 12/1997 | Evans et al. ............................. 604/264 |
| 5,797,849 | 8/1998 | Vesely et al. ............................ 600/461 |
| 5,846,221 | 12/1998 | Snoke et al. ............................... 604/49 |

FOREIGN PATENT DOCUMENTS

| | | |
|---|---|---|
| WO 97/45129 | 12/1997 | WIPO . |
| WO 97/45130 | 12/1997 | WIPO . |
| WO 97/45131 | 12/1997 | WIPO . |

OTHER PUBLICATIONS

Mandai, et al., "Direct Thrombosis of Aneurysms with Cellulose Acetate Polymer", *J. Neurosurg.*, 77:497–500 (1992).

Kinugasa, et al., "Direct Thrombosis of Aneurysms with Cellulose Acetate Polymer", *J. Neurosurg.*, 77:501–507 (1992).

Casarett and Doull's Toxicology, Amdur, et al., Editors, Pergamon Press, New York, pp. 661–664 (1975).

Kinugasa, et al., "Early Treatment of Subarachnoid Hemorrhage After Preventing Rerupture of an Aneurysm", *J. Neurosurg.*, 83:34–41 (1995).

Kinugasa, et al., "Phrophylactic Thrombosis to Prevent New Bleeding and to Delay Aneurysm Surgery", *Neurosurg.*, 36:661 (1995).

Taki, et al., "Selection and Combination of Various Endovascular Techniques in the Treatment of Giant Aneurysms", *J. Neurosurg.*, 77:37–42 (1992).

Castaneda–Zuniga, et al., *Interventional Radiology*, in Vascular Embolothereapy, Part 1, 1:9–32, Williams & Wilkins, Publishers (1992).

Goodwin, et al., "Preliminary Experience with Uterine Artery Embolization for Uterine Fibroids", *J. Vasc. Interven. Radiol.* 8:517–526 (1997).

Vedantham, et al., "Uterine artery embolization: An underused method of controlling pelvic hemorrhage", *Am. J. Obstet. Gynecol.* 176(4):938–948 (1997).

Tranbahuy, et al., "Direct Intratumoral Embolization of Juvenile Angiofibroma", *Am. J. Otolaryng.* 15(6):429–435 (1994).

(List continued on next page.)

*Primary Examiner*—Wynn Wood Coggins
*Assistant Examiner*—Deborah Blyveis
*Attorney, Agent, or Firm*—Burns, Doane, Swecker & Mathis, LLP

[57] ABSTRACT

This invention is directed to novel methods for gynecologic embolotherapy. The methods directly access the blood vessels to be embolized transcervically rather than arterially. The methods provide precise directed delivery of embolizing compositions, and are particularly suited for treating uterine fibroids. Kits containing one or more devices for transcervical injection and an embolizing composition are also provided. In a preferred embodiment, fluid embolizing compositions are used. In a more preferred embodiment, these fluid embolic compositions comprise a biocompatible polymer, a biocompatible solvent and a biocompatible water insoluble contrast agent. In a most preferred embodiment, the contrast agent is characterized by having an average particle size of about 10 μm or less.

14 Claims, 1 Drawing Sheet

OTHER PUBLICATIONS

Casasco, et al., "Devascularization of Craniofacial Tumors by Percutaneous Tumor Puncture", *Am. J. Neuroradiol.* 15:1233–1239 (1994).

Sutton, et al., "Treatment of Large Uterine Fibroids", *British J. Obst. Gyna.* pp. 494–496 (1996).

Ravina, et al., *Contracept. Fertil. Sex*, 28(1):45–49 (1995) (English Abstract Only).

"Unmet Needs in Gynecological Surgery", *MedPro Month*, 7(10)261–265 (Oct. 1997).

Roan, Science File, "Alternatives to Hysterectomy".

GYNECOLOGIC EMBOLOTHERAPY METHODS

BACKGROUND OF THE INVENTION

1. Field of the Invention

This invention is directed to novel methods for gynecologic embolotherapy. The methods of this invention specifically access the blood vessels to be embolized transcervically rather than arterially. The methods provide precise directed delivery of embolizing compositions, and are particularly suited for treating uterine fibroids.

Kits containing one or more devices for transcervical injection and an embolizing composition are also provided. In a preferred embodiment, fluid embolizing compositions are used. In a more preferred embodiment, these fluid embolic compositions comprise a biocompatible polymer, a biocompatible solvent and a biocompatible water insoluble contrast agent. In a most preferred embodiment, the contrast agent is characterized by having an average particle size of about 10 µm or less.

REFERENCES

The following publications are cited in this application as superscript numbers:

[1] Mandai, et al., "Direct Thrombosis of Aneurysms with Cellulose Acetate Polymer", *J. Neurosurg.*, 77:497–500 (1992)

[2] Kinugasa, et al., "Direct Thrombosis of Aneurysms with Cellulose Acetate Polymer", *J. Neurosurg.*, 77:501–507 (1992)

[3] Casarett and Doull's *Toxicology*, Amdur et al., Editors, Pergamon Press, New York, pp. 661–664 (1975)

[4] Greff, et al., U.S. Pat. No. 5,667,767 for "Novel Compositions for Use in Embolizing Blood Vessels", issued Sep. 16, 1997

[5] Greff, et al., U.S. Pat. No. 5,580,568 for "Cellulose Diacetate Compositions for Use in Embolizing Blood Vessels", issued Dec. 3, 1996

[6] Kinugasa, et al., "Early Treatment of Subarachnoid Hemorrhage After Preventing Rerupture of an Aneurysm", *J. Neurosurg.*, 83:34–41 (1995)

[7] Kinugasa, et al., "Prophylactic Thrombosis to Prevent New Bleeding and to Delay Aneurysm Surgery", *Neurosurg.*, 36:661 (1995)

[8] Taki, et al., "Selection and Combination of Various Endovascular Techniques in the Treatment of Giant Aneurysms", *J. Neurosurg.*, 77:37–42 (1992)

[9] Evans, et al., U.S. patent application Ser. No. 08/802,252 for "Novel Compositions for Use in Embolizing Blood Vessels", filed Feb. 19, 1997.

[10] Castaneda-Zuniga, et al., *Interventional Radiology*, in Vascular Embolotherapy, Part 1, 1:9–32, Williams & Wilkins, Publishers (1992)

[11] Rabinowitz, et al., U.S. Pat. No. 3,527,224, for "Method of Surgically Bonding Tissue Together", issued Sep. 8, 1970

[12] Hawkins, et al., U.S. Pat. No. 3,591,676, for "Surgical Adhesive Compositions", issued Jul. 6, 1971

[13] Evans, et al., U.S. Pat. Application Ser. No. 08/655,987, for "Methods for the Reversible Sterilization of Male Mammals, filed May 31, 1996

[14] Evans, et al., U.S. Pat. Application Ser. No. 08/656,394, for "Methods for the Reversible Sterilization of Female Mammals, filed May 31, 1996

[15] Evans, et al., U.S. Pat. No. 5,695,480, for "Novel Embolizing Compositions, issued Dec. 9, 1997

[16] Goodwin, et al., "Preliminary Experience with Uterine Artery Embolization for Uterine Fibroids," *J. Vasc. Interven. Radiol.* 8:517–526 (1997)

[17] Vedantham, et al., "Uterine artery embolization: An underused method of controlling pelvic hemorrhage," *Am. J. Obstet. Gynecol.* 176(4):938–948 (1997)

[18] Tranbahuy, et al., "Direct Intratumoral Embolization of Juvenile Angiofibroma," *Am. J. Otolaryng.* 15(6):429–435 (1994)

[19] Casasco, et al., "Devascularization of Craniofacial Tumors by Percutaneous Tumor Puncture," *Am. J. Neuroradiol.* 15:1233–1239 (1994)

The disclosures of each of the above publications, patents and patent application are herein incorporated by reference in their entirety to the same extent as if the language of each individual publication, patent and patent application were specifically and individually included herein.

2. Background of the Invention

Gynecologic embolotherapy may be conducted for a variety of purposes including the treatment of postpartum and postcaesarean bleeding, the treatment of postsurgical vaginal bleeding, the prevention and/or treatment of hemorrhage from ectopic pregnancy, prophylactically prior to myomectomy and in obstetrical patients at high risk for bleeding, such as those patients with placenta previa, placenta accreta, uterine fibroids and twin fetal death. Gynecological embolotherapy, however, has only been used for non-malignant conditions and the literature reports the use of polyvinyl alcohol (PVA) particles of sizes varying from 150 to 700 µm as the embolizing agents.[16]

Complications arising from endovascular embolization using PVA particles include complications of angiography, pelvic infection, pelvic pain and ischemia.[16] Notwithstanding the use of PVA particles as the embolizing agent, uterine fibroid shrinkage was noted in patients with fibroids following gynecological embolization of these patients for acute bleeding, leading to the establishment of several clinical programs which use uterine artery embolization for the treatment of uterine fibroids. Clinical success of uterine artery embolization (defined as improvement in bleeding, pain and mass effect such that no further operative therapy is required) is good. Fibroid size is reduced, on average, by about 50% in patients undergoing uterine artery embolization.[16,17]

In view of the above, better gynecological embolization methods for treatment and/or prevention of gynecological and/or obstetrical bleeding disorders which provide precise directed embolization are needed. In particular, techniques which are minimally invasive and which could be performed in a gynecologist's office or an outpatient setting would be ideal.

This invention is directed to the use of embolization methods which directly access the blood vessels to be embolized transcervically rather than arterially. These methods, of course, are less invasive and, accordingly, better tolerated as compared to intravascular embolization techniques.

Heretofore, embolization methods preferably included the use of a water insoluble, radiopaque contrast agent in the embolizing compositions in order that the physician can visualize delivery of the composition typically by microcatheter to the vascular site via conventional techniques such as fluoroscopy.[1-8] Additionally, the use of water insoluble contrast agents is beneficial during posttreatment procedures to visualize the embolized mass during, for example, surgery or to monitor the disease condition and/or for retreatment purposes. Visualization is particularly necessary when using catheter delivery techniques in order to ensure both that the composition is being delivered to the intended vascular site and that the requisite amount of composition is delivered. Preferably, the water insoluble contrast agent has an average particle size of about 10 μm or less.[15]

In addition to the above, intratumoral embolization of vertebral bone tumors, craniofacial tumors and juvenile angiofibroma prior to surgical removal of tumor is known.[18,19] Such embolization methods avoid the non-selective embolization of primary or secondary branch arteries and may be used even after ligation of feeding pedicles.

SUMMARY OF THE INVENTION

As noted above, this invention is directed to the use of embolization methods which directly access the blood vessels to be embolized transcervically rather than arterially. The methods provide precise directed delivery of embolizing compositions using minimally invasive procedures, and are particularly suited for treating uterine fibroids. Kits containing one or more devices for transcervical injection and an embolizing composition are also provided.

In a preferred embodiment, fluid embolizing compositions are used. In one preferred embodiment, these fluid embolic compositions comprise a biocompatible polymer, a biocompatible solvent and a contrast agent. In another preferred embodiment, these fluid embolic compositions comprise a biocompatible prepolymer and a contrast agent. In a most preferred embodiment, the contrast agent is characterized by having an average particle size of about 10 μm or less.

Accordingly, in one aspect the invention provides a method for gynecological embolization comprising:

inserting a catheter capable of penetrating a blood vessel through the cervix into the uterus using an instrument which allows visualization of the uterine wall;

inserting the catheter through the cervix and into a blood vessel to be embolized;

and delivering an embolic material through the catheter into the vessel under conditions wherein said blood vessel is embolized.

A hysteroscope may preferably be used to insert the catheter, which preferably is needle tipped. The vessel may preferably be a blood vessel of a uterine fibroid. The embolic material may be a sclerosing agent, such as ethanol or hot fluids; a particulate, such as polyvinyl alcohol (PVA); or, preferably, a fluid embolizing substance.

Methods further comprising the step of delivering a detectable agent, such as a contrast agent, through the catheter after it has been inserted into the vessel and detecting the agent to confirm that the catheter has the proper placement prior to delivery of embolic material to the vessel are also provided.

In another aspect, the invention provides a kit of parts comprising:

a device which allows catheter insertion and visualization of the uterine wall;

a catheter capable of penetrating a blood vessel to be embolized;

a catheter capable of delivering an embolic material; and an embolic material.

A hysteroscope may preferably be the catheter insertion/visualization device. The catheter may preferably be needle tipped, and a single catheter may be used both for vessel penetration and embolizing composition delivery. The embolic material may be a sclerosing agent, such as ethanol; a particulate, such as PVA; or, preferably, a fluid embolizing substance. Kits further comprising a detectable agent, such as a contrast agent, are also provided.

BRIEF DESCRIPTION OF THE DRAWING FIGURES

The invention will be described in greater detail with references to the accompanying drawing in which like elements bear like reference numerals, and wherein:

FIG. 1 is a cross-sectional view of a uterus with a hysteroscope placed in the uterus according to the present invention.

DETAILED DESCRIPTION OF THE INVENTION

Figure 1:
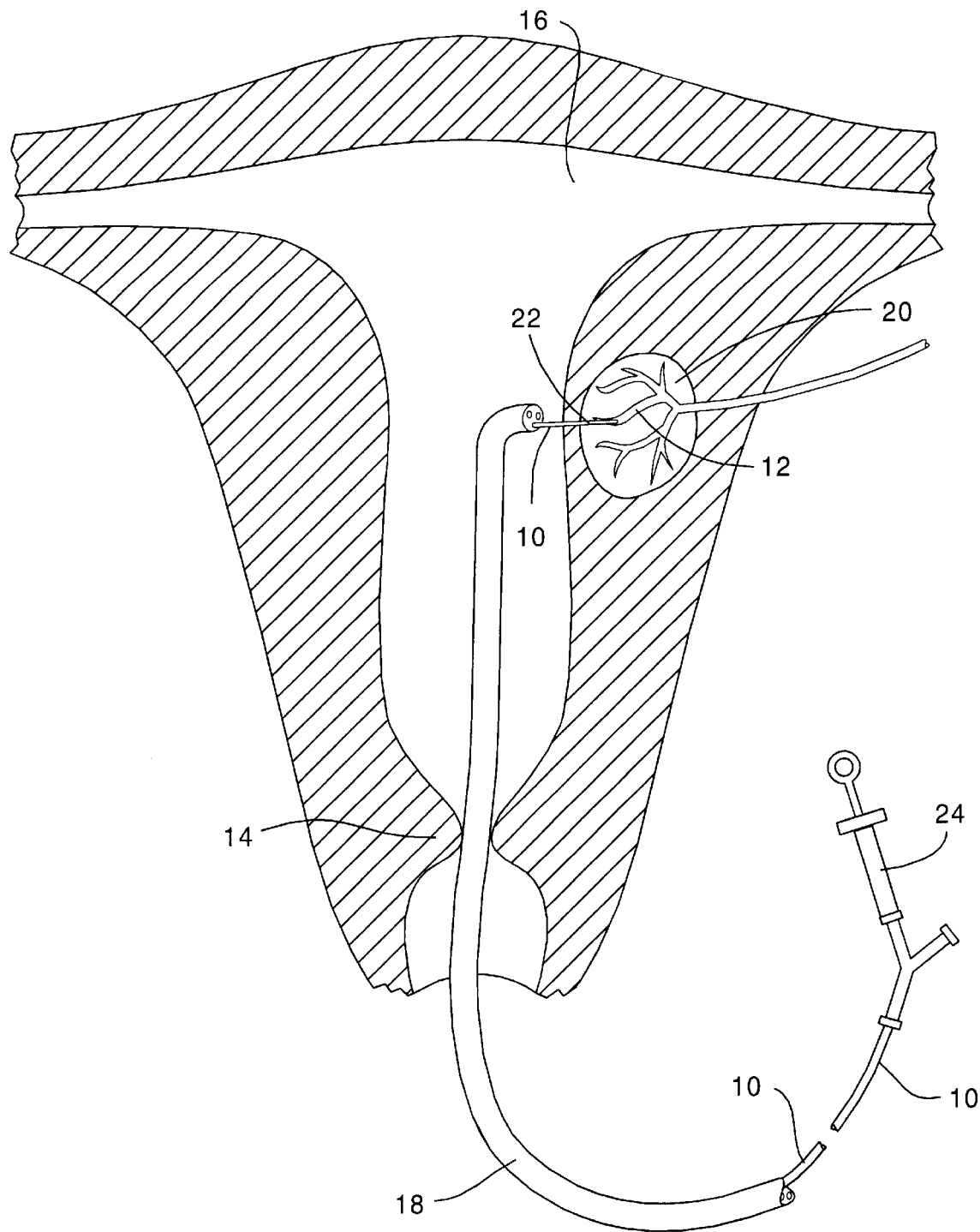

This invention is directed to novel gynecological embolization methods which directly access the vessels to be embolized transcervically rather than arterially. The methods provide precise directed delivery of embolizing compositions using minimally invasive procedures, and are particularly suited for treating uterine fibroids.

However, prior to discussing this invention in further detail, the following terms will first be defined:

The term "embolizing" refers to a process wherein a material is injected into a blood vessel which fills or plugs the vessel and/or encourages clot formation so that blood flow in the vessel ceases. Embolization of the blood vessel is, therefore, important in preventing/controlling bleeding due to lesions. In addition, embolization can be used to ablate diseased tissue (e.g., tumors, etc.) by cutting off its blood supply. Embolization may also be used to prevent blood loss during or immediately following surgery. Embolization of tumors may be performed preoperatively to shrink tumor size and to aid in visualization of the tumor as well as to prevent blood loss related to surgical procedures.

"Gynecological embolization" refers to embolization used to control acute and chronic genital bleeding in a wide variety of obstetric and gynecological disorders, including uterine fibroids.

The term "biocompatible polymer" refers to polymers which, in the amounts employed, are non-toxic, chemically inert, and substantially non-immunogenic when used internally in the patient and which are substantially insoluble in blood. Suitable biocompatible polymers include, by way of example, cellulose acetates[2,6-7] (including cellulose diacetate[5]), ethylene vinyl alcohol copolymers[4,8], hydrogels (e.g., acrylics), polyacrylonitrile, polyvinylacetate, cellulose acetate butyrate, nitrocellulose, copolymers of urethane/carbonate, copolymers of styrene/maleic acid, and mixtures thereof.[9] Preferably, the biocompatible polymer is also non-inflammatory when employed in situ.

The particular biocompatible polymer employed is not critical and is selected relative to the viscosity of the resulting polymer solution, the solubility of the biocompatible polymer in the biocompatible solvent, and the like. Such factors are well within the skill of the art.

Preferred biocompatible polymers include cellulose diacetate and ethylene vinyl alcohol copolymer. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the embolizing properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 6 weight percent of the ethylene vinyl alcohol copolymer, 35 weight percent of a tantalum contrast agent in DMSO has a viscosity equal to or less than 60 centipoise at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous solution (e.g., blood). In a particularly preferred embodiment, the copolymers employed herein comprise a mole percent of ethylene of from about 25 to about 60 and a mole percent of vinyl alcohol of from about 40 to about 75. These compositions provide for requisite precipitation rates suitable for use in embolizing blood vessels in gynecological embolization procedures.

The term "contrast agent" refers to a biocompatible (non-toxic) radiopaque material capable of being monitored during injection into a mammalian subject by, for example, radiography or fluoroscopy. The contrast agent can be either water soluble or water insoluble. Examples of water soluble contrast agents include metrizamide, iopamidol, iothalamate sodium, iodomide sodium, and meglumine.

The term "water insoluble contrast agent" refers to a water insoluble (i.e., has a water solubility of less than 0.01 mg/ml at 20° C.), radiopaque material capable of being monitored during injection into a mammalian subject by, for example, radiography. Examples of water insoluble contrast agents include tantalum, tantalum oxide and barium sulfate, which are commercially available in the proper form for in vivo use. Methods for preparing such water insoluble biocompatible contrast agents having an average particle size of about 10 μm or less are described below. Other water insoluble contrast agents include gold, tungsten and platinum.

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, acetone, and the like. Aqueous mixtures with the biocompatible solvent can also be employed provided that the amount of water employed is sufficiently small that the dissolved polymer precipitates upon contact with the blood. Preferably, the biocompatible solvent is dimethylsulfoxide (DMSO).

The term "encapsulation" as used relative to the contrast agent being encapsulated in the polymer precipitate is not meant to infer any physical entrapment of the contrast agent within the precipitate much as a capsule encapsulates a medicament. Rather, this term is used to mean that an integral coherent precipitate forms which does not separate into individual components.

The term "biocompatible prepolymer" refers to materials which polymerize in situ to form a polymer and which, in the amounts employed, are non-toxic, chemically inert, and substantially non-immunogenic when used internally in the patient and which are substantially insoluble in blood. Suitable biocompatible prepolymers include, by way of example, cyanoacrylates[10,11,12], hydroxyethyl methacrylate, silicon prepolymers, and the like. The prepolymer can either be a monomer or a reactive oligomer[12]. Preferably, the biocompatible prepolymer is also non-inflammatory when employed in situ.

Compositions

Any conventional embolizing material may be used in the methods of the present invention. The requirements are that such materials may be delivered through the catheter to the vasculature to be embolized and that they are biocompatible. Because in many cases smaller catheters will be used for delivery of embolizing materials to smaller vessels, smaller particle sizes of particulate embolizing materials are preferred. However, such small particles can be visualized under fluoroscopy and, accoridngly, migrate during injection can cause unwanted ischemia and necrosis.[17] Small particles such as PVA can compact and migrate resulting in incomplete embolization.

Therefore embolizing compositions which contain small particles but which provide for a solid coherent in vivo, such as those described below, are preferably used. Selection of a suitable embolizing material is known to those of skill in the art.

The embolization composition can comprise either a biocompatible polymer or prepolymer. For example, the polymer compositions preferably employed in the methods of this invention are prepared by conventional methods whereby each of the components is added and the resulting composition mixed together until the overall composition is substantially homogeneous.

For example, polymer compositions can be prepared by adding sufficient amounts of the biocompatible polymer to the biocompatible solvent to achieve the effective concentration for the polymer composition. Preferably, the polymer composition will comprise from about 2.5 to about 8.0 weight percent of the biocompatible polymer composition based on the total weight of the polymer composition and more preferably from about 4 to about 5.2 weight percent. If necessary, gentle heating and stirring can be used to effect dissolution of the biocompatible polymer into the biocompatible solvent, e.g., 12 hours at 50° C.

Sufficient amounts of the contrast agent are then added to the biocompatible solvent to achieve the effective concentration for the complete composition. Preferably, the composition will comprise from about 10 to about 40 weight percent of the contrast agent and more preferably from about 20 to about 40 weight percent and even more preferably about 30 weight percent. When the contrast agent is not soluble in the biocompatible solvent, stirring is employed to effect homogeneity of the resulting suspension. In order to enhance formation of the suspension, the particle size of the insoluble contrast agent is preferably maintained at about 10 μm or less and more preferably at from about 1 to about 5 μm (e.g., an average size of about 2 μm). In one preferred embodiment, the appropriate particle size of the contrast agent is prepared, for example, by fractionation. In such an embodiment, a water insoluble contrast agent such as tantalum having an average particle size of less than about 20 microns is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition is heat sterilized and then stored preferably in sealed amber bottles or vials until needed.

Each of the polymers recited herein is commercially available but can also be prepared by methods well known in the art. For example, polymers are typically prepared by conventional techniques such as radical, thermal, UV, γ irradiation, or electron beam induced polymerization employing, as necessary, a polymerization catalyst or polymerization initiator to provide for the polymer composition. The specific manner of polymerization is not critical and the polymerization techniques employed do not form a part of this invention.

In order to maintain solubility in the biocompatible solvent, the polymers described herein are preferably not cross-linked.

When the embolization composition comprises a prepolymer, such prepolymer compositions can be prepared by adding sufficient amounts of the contrast agent to the solution (e.g., liquid prepolymer) to achieve the effective concentration for the complete prepolymer composition. Preferably, the prepolymer composition will comprise from about 10 to about 40 weight percent of the contrast agent and more preferably from about 20 to about 40 weight percent and even more preferably about 30 weight percent. When the contrast agent is not soluble in the biocompatible prepolymer composition, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm).

When the prepolymer is liquid, the use of a biocompatible solvent is not absolutely necessary but may be preferred to provide for an appropriate viscosity, etc. in the embolic composition. Preferably, when employed, the biocompatible solvent will comprise from about 30 to about 90 weight percent of the biocompatible prepolymer composition based on the total weight of the prepolymer composition and more preferably from about 60 to about 80 weight percent. When a biocompatible solvent is employed, the prepolymeric composition typically comprises from about 10 to about 50 weight percent of the prepolymer based on the total weight of the composition.

In a particularly preferred embodiment, the prepolymer is a cyanoacrylate ester which is preferably employed in the absence of a biocompatible solvent. When so employed, the cyanoacrylate composition is selected to have a viscosity of from about 5 to about 20 centipoise at 20° C.

The particular order of addition of components is not critical and stirring of the resulting suspension is conducted as necessary to achieve homogeneity of the composition. Preferably, mixing/stirring of the composition is conducted under an anhydrous atmosphere at ambient pressure. The resulting composition is sterilized and then stored preferably in sealed amber bottles or vials until needed.

When the contrast agent employed in the polymer or prepolymer composition is less than about 100 μm in average particle size, the composition is sometimes referred to herein as a "fluid composition".

Methods

Suitable embolizing compositions such as those described above can be employed in the claimed methods for gynecological embolization of blood vessels. In the claimed methods, and as shown in FIG. 1 a catheter reference number 10 capable of penetrating a vessel 12 to be embolized, such as a needle tipped (20 G) catheter (3–5 French), is inserted through the cervix 14 into the uterus 16 using a device, 18 such as a hysteroscope, which allows visualization of the uterine wall. Generally, the patient is prepared in the usual manner for a hysteroscopic procedure, and warm saline is infused to inflate the uterus and help visualize the uterine wall using the hysteroscope, then the catheter 10 is inserted through the scope 18. The vessel 12 to be embolized is located and the catheter 10 inserted through the uterine wall and placed in the vessel 12, e.g., the position of a uterine fibroid 20 is determined and the needle tip 22 of the catheter 10 placed in a blood vessel 12 feeding or within the fibroid mass 20.

In a preferred method, a detectable contrast agent is injected by syringe 24 through the catheter 10 and, using, e.g., fluoroscopy, the needle tip positioned into the desired vasculature. When the tip of the catheter is positioned as desired, an embolic material is injected to precisely embolize the desired vessel(s). Repeated placement of the catheter 10, contrast injection and embolization may be needed to completely embolize the vasculature of, e.g., a uterine fibroid 20 or tumor tissue.

In such methods, a sufficient amount of embolizing composition is introduced into the selected blood vessel 12 via a catheter delivery means 10, preferably under fluoroscopy, so that the blood vessel is embolized. The particular amount of embolizing composition employed is dictated by the total volume of the vasculature to be embolized, the concentration of polymer/prepolymer in the composition, the rate of precipitation (solids formation) of the polymer, etc. Such factors are well within the skill of the art.

One particularly preferred method for catheter delivering the embolizing compositions of this invention to the selected vascular site is via a small diameter medical catheter. The particular catheter employed is not critical provided that polymeric catheter components are compatible with the embolizing composition (i.e., the catheter components will not readily degrade in the embolizing composition). In this regard, it is preferred to use polyethylene in the catheter components because of its inertness in the presence of the embolizing composition described herein. Other materials compatible with the embolizing compositions can be readily determined by the skilled artisan and include, for example, other polyolefins, fluoropolymers (e.g., Teflon™), silicone, etc.

When a polymer composition is introduced into the vascular site, the biocompatible solvent diffuses rapidly into the blood and a solid precipitate forms which precipitate is the water insoluble polymer with the contrast agent encapsulated therein. Without being limited to any theory, it is believed that initially, a soft gel to spongy solid precipitate forms upon contact with the blood. This precipitate then restricts blood flow, entrapping red cells thereby causing clot embolization of the blood vessel.

When a prepolymer composition is introduced into the vascular site, the prepolymer rapidly polymerizes and a solid biocompatible polymer forms in the blood vessel which polymer embolizes the blood vessel. Without being limited to any theory, it is believed that initially, a soft gel to spongy solid precipitate forms upon contact with the blood. This precipitate then restricts blood flow, entrapping red cells thereby causing clot embolization of the blood vessel.

Utility

The methods described herein are useful in gynecological embolization to prevent/control bleeding related to gynecological and/or obstetrical conditions. Accordingly, these compositions find use in human and other mammalian subjects requiring such embolization of blood vessels. Additionally, the methods can be used in the reversible sterilization of mammalian patients as described in concurrently filed applications by Evans, et al.[13,14].

The following examples are set forth to illustrate the claimed invention and are not to be construed as a limitation thereof.

EXAMPLES

Unless otherwise stated, all temperatures are in degrees Celsius. Also, in these examples and elsewhere, the following abbreviations have the following meanings:

cc=cubic centimeter
cm=centimeter
DMSO=dimethylsulfoxide
EVOH=ethylene vinyl alcohol copolymer
g=gram
ID=internal diameter
in.=inch
min.=minute
mL=milliliter
mm=millimeter
OD=outer diameter
sec.=seconds
μm=micron Example 1

In a gynecologist's office, a patient suffering from excessive vaginal bleeding due to uterine fibroids is prepared in the usual manner for a hysteroscopic procedure. Warm saline is infused to inflate the uterus and help visualize the uterine wall using the hysteroscope 18, then a needle tipped (20 G) catheter 10 (5 French in size) is inserted through the scope 18 so that it is inserted through the cervix 14 and into the uterus 16 of the patient.

The position of a uterine fibroid 20 is determined and the needle tip of the catheter 10 placed in a blood vessel 12 within the fibroid mass 20. An aqueous based iodinated contrast agent is injected by syringe 24 through the catheter 10 and then the needle tip 22 is positioned into the desired vasculature. Using fluoroscopy, a flow of contrast agent is used to determine proper placement of the catheter 10.

When the tip 22 of the catheter 10 is positioned as desired, a liquid embolic material under fluoroscopic digital roadmapping is injected to precisely embolize the desired vessel (s) in the fibroid 20. Repeated placement of the catheter 10, contrast injection and embolization is performed until the vasculature of the uterine fibroid 20 is completely embolized.

From the foregoing description, various modifications and changes in the composition and method will occur to those skilled in the art. All such modifications coming within the scope of the appended claims are intended to be included therein.

What is claimed is:

1. A method for gynecological embolization comprising:
   (a) inserting a catheter capable of penetrating a blood vessel through the cervix into the uterus using a device which allows visualization of the uterine wall;
   (b) inserting the catheter through the cervix and into a blood vessel to be embolized; and
   (c) delivering an embolic material through the catheter into the vessel.

2. The method of claim 1 wherein said device allowing visualization is a hysteroscope.

3. The method of claim 1 wherein said catheter is needle tipped.

4. The method of claim 1 wherein the blood vessel is a blood vessel of a uterine fibroid.

5. The method of claim 1 wherein the embolic material is selected from the group consisting of sclerosing embolic materials, particulate embolic materials and fluid embolic materials.

6. The method of claim 1 further comprising the steps of:
   (a) delivering a detectable agent through the catheter after it has been inserted into the vessel; and
   (b) detecting the agent to confirm that the catheter has the proper placement in the vessel prior to delivery of embolic material.

7. The method of claim 1 wherein the embolizing composition is a fluid embolizing composition comprising:
   (a) from about 2.5 to about 8.0 weight percent of a biocompatible polymer;
   (b) from about 10 to about 40 weight percent of a water insoluble, biocompatible contrast agent having an average particle size of about 10 μm or less; and
   (c) from about 52 to about 87.5 weight percent of a biocompatible solvent
   wherein the weight percent of the polymer, contrast agent and biocompatible solvent is based on the total weight of the complete composition.

8. The method according to claim 7 wherein said biocompatible solvent is selected from the group consisting of dimethylsulfoxide, ethanol and acetone.

9. The method according to claim 8 wherein said biocompatible solvent is dimethylsulfoxide.

10. The method according to claim 7 wherein said water insoluble contrast agent is selected from the group consisting of tantalum, tantalum oxide, tungsten and barium sulfate.

11. The method according to claim 10 wherein said contrast agent is tantalum.

12. The method according to claim 7 wherein said biocompatible polymer is selected from the group consisting of cellulose acetates, ethylene vinyl alcohol copolymers, hydrogels, polyacrylonitrile, polyvinylacetate, cellulose acetate butyrate, nitrocellulose, copolymers of urethane/carbonate, copolymers of styrene/maleic acid, and mixtures thereof.

13. The method according to claim 12 wherein said biocompatible polymer is an ethylene and vinyl alcohol copolymer.

14. The method according to claim 13 wherein said contrast agent has an average particle size of from 1 to 10 microns.

* * * * *